US00PP13492P3

(12) United States Plant Patent
Lemon

(10) Patent No.: US PP13,492 P3
(45) Date of Patent: Jan. 21, 2003

(54) GERANIUM PLANT NAMED 'ELEGANCE ROSE BICOLOR'

(75) Inventor: David Lemon, County of Santa Barbara, CA (US)

(73) Assignee: Oglevee, Ltd., Connellsvillle, PA (US)

( * ) Notice: Subject to any disclaimer, the term of this patent is extended or adjusted under 35 U.S.C. 154(b) by 0 days.

(21) Appl. No.: 09/876,818

(22) Filed: Jun. 7, 2001

(65) Prior Publication Data

US 2002/0188990 P1 Dec. 12, 2002

(51) Int. Cl.[7] ..... A01H 5/00

(52) U.S. Cl. ..... Plt./331

(58) Field of Search ..... Plt./331

*Primary Examiner*—Bruce R. Campell
*Assistant Examiner*—Annette H. Para
(74) *Attorney, Agent, or Firm*—Webb Ziesenheim Logsdon Orkin & Hanson, P.C.

(57) ABSTRACT

A new and distinct early flowering regal geranium plant with red-purple and white bicolored petals above medium green foliage.

1 Drawing Sheet

CLASSIFICATION

*Pelargonium×domesticum* (regal geranium).

VARIETAL DENOMINATION

'Elegance Rose Bicolor'.

BACKGROUND OF THE INVENTION

The present invention comprises a new and distinct cultivar of *Pelargonium×domesticum* known by the varietal name 'Elegance Rose Bicolor'. The new variety was discovered in a selected breeding program in Lompoc, Calif. The new variety is a selection from the cross of unpatented proprietary breed variety Seedling Salmon/blotch #245, the female parent and upatented proprietary breed variety Seedling Salmon/blotch #266, the male parent. The rose bicolor of the flowers of the new variety is distinct from other varieties in this market class. The new variety was first asexually reproduced by cuttings in Connellsville, Pa. The new variety has been trial and field tested at Connellsville and has been found to retain its distinctive characteristics and remain true to type through successive propagations.

The cultivar, when grown in a glass greenhouse in Connellsville, Pa. using natural light and temperatures of 60° F. night and 68° F. day, has a response time of 13 weeks from a rooted cutting to flowering in a 6 inch pot. The response time was determined on plants grown in soilless media employing constant fertilizer 150–200 parts per million of nitrogen and potassium in full light.

DESCRIPTION OF THE DRAWINGS

The accompanying photographic drawing illustrates the new variety, with the color being as nearly true as is possible with color illustrations of this type.

DESCRIPTION OF THE PLANT

The following detailed description sets forth the characteristics of the new cultivar at 10 weeks grown from a rooted cutting. The data which defines these characteristics were collected by asexual reproductions carried out by Oglevee, Ltd. in Connellsville, Pa. The color readings were taken on a plant under 200–220 foot candles of fluorescent cool white light. Color references are primarily to The R.H.S. Colour Chart of The Royal Horticultural Society of London.

PLANT

Form: Medium mound.
Height: 22–25 cm from soil to top of foliage.
Growth: Upright, free basal branching.
Strength: Does not require artifical support.
Foliage: Stalked leaf attachment; medium green foliage.
Rooting time: Roots visible to outside of artificial dirt plug in 14–21 days.
Leaves:
- *Size.*—Length: 7.2–9.4 cm. Width: 10–11.5 cm.
- *Shape.*—Reniform; truncate base.
- *Margin.*—Serrated; lobed.
- *Texture.*—Leathery; pubescent.
- *Color.*—Upper surface: Green Group 137A. Lower surface: Green Group 137C.
- *Ribs and veins.*—Venation: Palmate. Color: Yellow-Green Group 148C.

Petioles:
- *Color.*—Yellow-Green Group 148C.
- *Length.*—8–10.5 cm.

Stem:
- *Color.*—Yellow-Green Group 146C.
- *Internode length.*—0.5–3 cm.

THE BUD

Shape:
- *Overall.*—Elliptical to round cluster.
- *Individual bud.*—*Elliptical.*

Size:
- *Overall.*—4.5–5.5 cm across.
- *Individual bud.*—2.2–2.6 cm long; 1–1.2 cm wide.

Number of buds per cluster: 4–7.

INFLORESCENCE

Blooming habit: Continuous; large florets forming full flower heads.

*Size.*—12–14 cm.

*Borne.*—Flowers on umbel; umbel on pedicel; pedicel on peduncle.

Flowers:

*Form.*—Opened to slightly cupped; petals overlap; slightly ruffled.

*Number of flowers per umbel.*—4–7.

*Size.*—Diameter: 6.5–8 cm. Depth: 3–4 cm.

*Petals.*—Color: Upper surface: Lower Petals: Red-Purple Group 68C fading into Red-Purple Group 65D and then in White Group 155D. There is a brush of Red Group 53B present in the center of the lower petal. Upper Petals: There is a blotch of Greyed-Purple Group 187A in the center of the petal, fading into Red Group 50B towards the edge and turning into Red-Purple Group 63C at the edge. At the bottom of the blotch towards the base of the petal the color turns into Red-Purple Group 74A. The veins are very distinctively colored Greyed-Purple Group 187B and fading towards the edge. The base is White Group 155C. Lower surface: Lower Petals: Red Group 56D with a few dots of Red Group 55A shining through. Upper Petals: There is a blotch of Greyed-Red Group 187B in the center fading out to Greyed-Red Group 187C and then Red-Purple Group 66C. At the base of the blotch the color turns to Red-Purple Group 74B before it changes at the base to White Group 155C. The main veins are Red-Purple Group 68D. The other veins are Red-Purple Group 61B fading towards the edge. Shape: Obovate. Size: Length: 4.4–5 cm. Width: 3.3–4.7 cm. Margin: Entire. Number per floret: 5.

Texture and appearance: Smooth, satiny.

Tonality from a distance: Big rose pink flowers with distinct velvet eyes in the upper petals giving the umbel the bicolor apparance on medium green foliage.

Petaloids:

*Quantity.*—1–2.

*Shape.*—Twisted, tubular, irregular.

*Color.*—Red-Purple Group 68C with a dot of Red-Purple Group 60C.

Pedicel:

*Length.*—2.1–2.5 cm.

*Color.*—Yellow-Green Group 144A.

Peduncle:

*Length.*—9–9.5 cm.

*Color.*—Yellow-Green Group 144A.

Disease/pest resistance: No unusual susceptibility to diseases or pests has been noted to date.

Lasting quality: Individual umbels will last in the home environment for 4–6 weeks. Overrall flowering will continue as long as conditions remain cool at night with plenty of light provided.

Fragrance: None.

REPRODUCTIVE ORGANS

Stamens:

*Quantity.*—7.

*Anthers.*—3–4 mm.

*Filaments.*—Length: 1.7–2 cm. Color: Greyed-White Group 156D at the bottom changing into Red-Purple Group 62C at the top. Pollen: Golden orange.

Pistils:

*Number.*—One.

*Length.*—2.3–2.7 cm.

*Stigma.*—Number: One; five or six parted. Color: Greyed-Purple Group 187C.

*Style.*—Length: 1.2–1.4 cm. Color: Red-Purple Group 61A.

Ovaries:

*Completeness.*—Superior.

*Pubescence.*—Greatly pubescent.

*Length.*—7–8 mm.

*Width.*—3 mm.

*Color.*—Yellow-Green Group 145C.

Fruit: None observed.

GENERAL CHARACTERISTICS

1. 'Elegance Rose Bicolor' is a very early flowering plant.
2. Good plant type.
3. Good bicolor.

I claim:

1. A new and distinct variety of geranium plant substantially as shown and described.

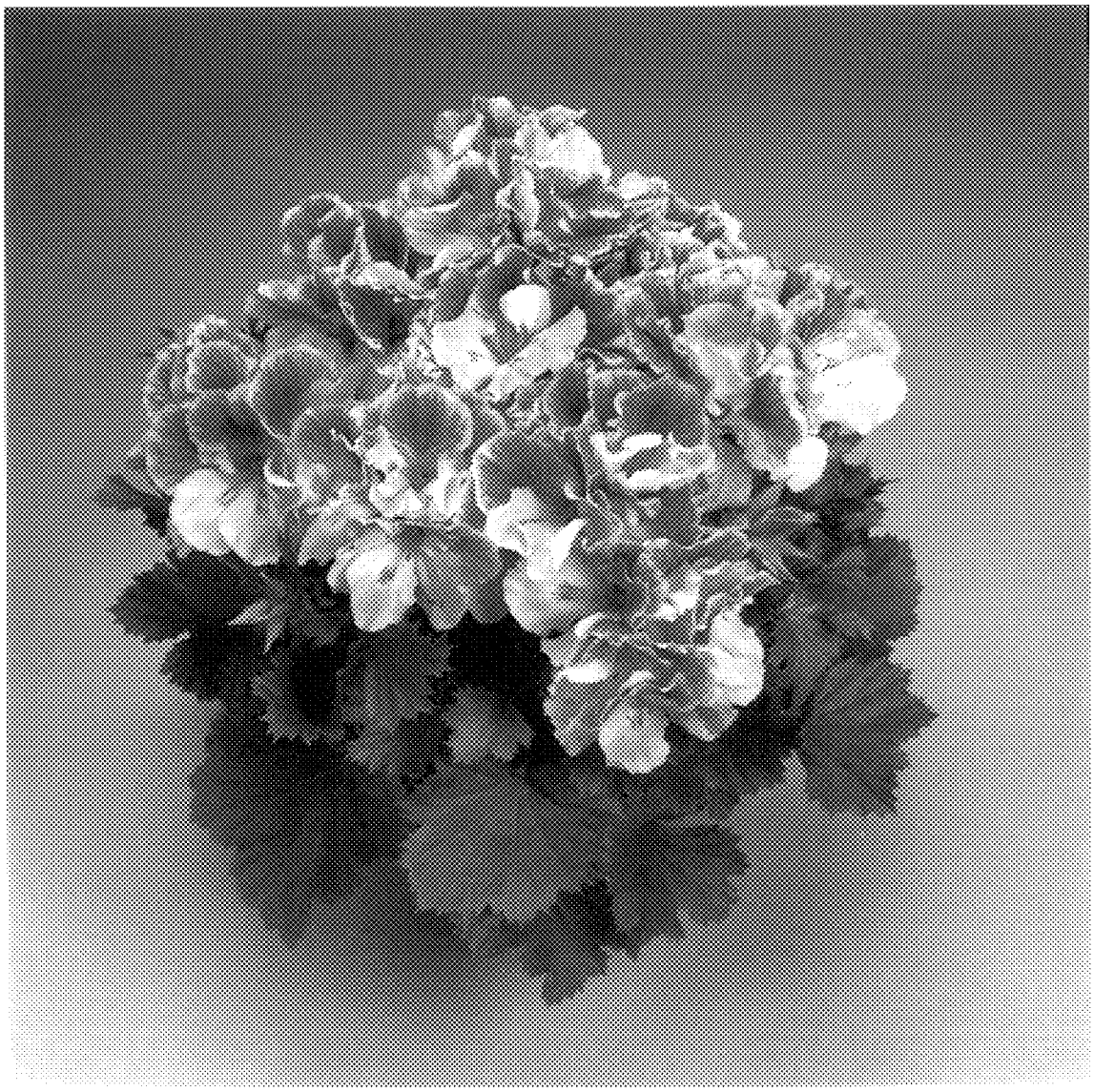

* * * * *